US00PP25676P3

(12) United States Plant Patent
Skelley

(10) Patent No.: US PP25,676 P3
(45) Date of Patent: Jul. 7, 2015

(54) *POTENTILLA FRUTICOSA* 'KM02'

(50) Latin Name: *Potentilla fruticosa*
Varietal Denomination: KM01

(71) Applicant: Kieran Skelley, Carbury (IE)

(72) Inventor: Kieran Skelley, Carbury (IE)

( * ) Notice: Subject to any disclaimer, the term of this patent is extended or adjusted under 35 U.S.C. 154(b) by 175 days.

(21) Appl. No.: 13/987,199

(22) Filed: Jul. 9, 2013

(65) Prior Publication Data

US 2014/0026268 P1 Jan. 23, 2014

(30) Foreign Application Priority Data

Jul. 20, 2012 (QZ) ..... PBR 20121621

(51) Int. Cl.
*A01H 5/00* (2006.01)
*A01H 5/02* (2006.01)

(52) U.S. Cl.
USPC ..... Plt./237
CPC ..... *A01H 5/0216* (2013.01)

(58) Field of Classification Search
USPC ..... Plt./237
See application file for complete search history.

*Primary Examiner* — Annette Para
(74) *Attorney, Agent, or Firm* — Cassandra Bright

(57) ABSTRACT

A new and distinct *Potentilla fruticosa* cultivar named 'KM01' is disclosed, characterized by early flowering and unique flower coloration. The new cultivar is a *Potentilla fruticosa* suitable as an ornamental garden or container plant.

2 Drawing Sheets

Figure 1:
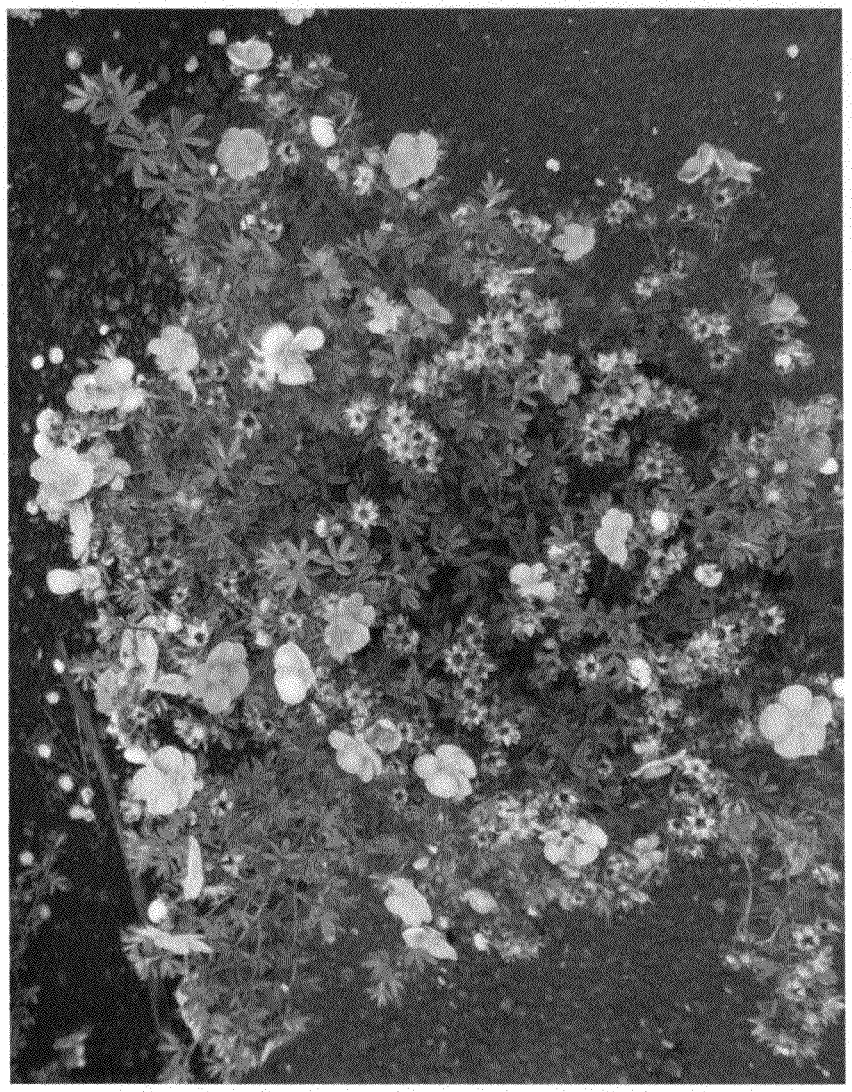

Latin name of the genus and species: *Potentilla fruticosa.*
Variety denomination: 'KM01'.

BACKGROUND OF THE INVENTION

The new cultivar is a chance, whole plant mutation selected by the inventor, Keiran Skelley, a citizen of the Republic of Ireland, in June of 2007 at the breeder's nursery located near Carbury, Ireland. 'KM01' was found as a single, whole plant mutation growing in a planting of the parent plant, the unpatented variety of *Potentilla fruticosa* 'Daydawn'. The genus *Potentilla* has recently been changed to *Dasiphora* within the European Union. For the purpose of this US plant patent application, however, the applicant refers to the variety by the Genus name currently accepted in North America.

Asexual reproduction of the new cultivar 'KM01' was first performed by vegetative cuttings by the breeder in Carbury, Ireland during May of 2008. The inventor kept the plants in a confidential, restricted location, observing plant habit and stability. Subsequent propagation of 5 generations of these plants have shown that the unique features of this cultivar are stable and reproduced true to type.

SUMMARY OF THE INVENTION

The cultivar 'KM01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KM01'. These characteristics in combination distinguish 'KM01' as a new and distinct *Potentilla* cultivar:

1. Pronounced dark edges to the petals of young flowers.
2. Multi-color petals of apricot, peach and dark pink coloration
3. Flower petals colored with a darker margin.
4. Earlier flowering than other varieties, including the parent.

PARENT COMPARISON

Plants of the new cultivar 'KM01' are similar to plants of the parent variety, *Potentilla fruticosa* 'Daydawn' in most horticultural characteristics, however, plants of 'KM01' are slightly more compact than those of the parent variety. Plants of 'KM01' begin flowering up to 14 days earlier than plants of the parent variety. Additionally the flower of 'KM01' produce multi-color petals of apricot, peach and dark pink coloration with darker margin whereas the parent variety produces a flower of yellow-peach petal coloration.

COMMERCIAL COMPARISON

'KM01' can be compared to the patented commercial variety *Potentilla fruticosa* 'Pink Beauty', U.S. Plant Pat. No. 9,874. Plants of 'Pink Beauty' are similar to plants of 'KM01' in most horticultural characteristics, however, plants of 'KM01' are more upright and produce multicolored flowers with a single row of petals, whereas plants of 'Pink Beauty' produce single colored flowers with a double row of petals.

'KM01' can be compared to the unpatented commercial variety *Potentilla fruticosa* 'Glenroy Pinkie', unpatented. Plants of 'Glenroy Pinkie' are similar to plants of 'KM01' in most horticultural characteristics, however, plants of 'KM01' produce multicolored flowers, whereas plants of 'Glenroy Pinkie' produce single colored flowers.

BRIEF DESCRIPTION OF THE PHOTOGRAPHS

The accompanying photograph in FIG. 1 illustrates in full color a typical plant of 'KM01' grown outdoors This plant is approximately 3 years old. The photograph was taken using conventional techniques and although colors may appear different from actual colors due to light reflectance it is as accurate as possible by conventional photographic techniques.

Figure 2:
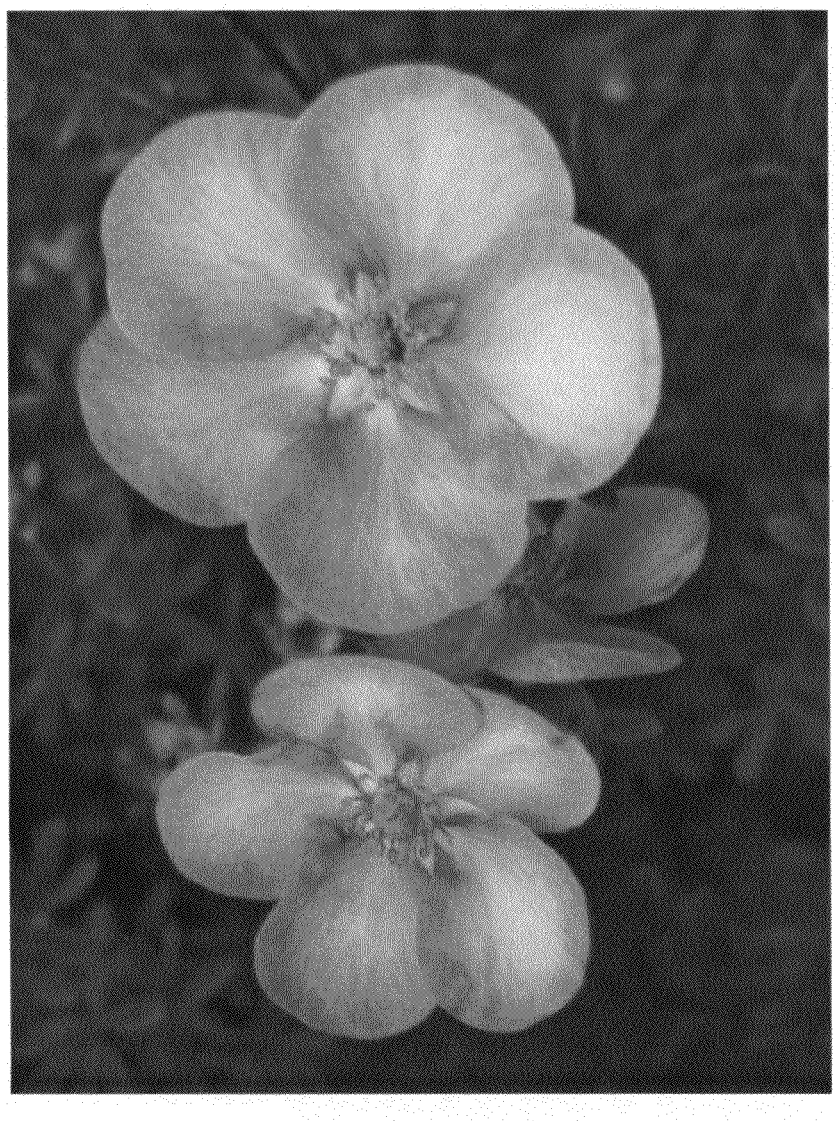

FIG. 2 illustrates in full color typical flowers of 'KM01'.

DETAILED BOTANICAL DESCRIPTION

In the following description, color references are made to The Royal Horticultural Society Colour Chart, 2007 except where general terms of ordinary dictionary significance are used. The following observations and measurements describe 'KM01' plants grown outdoors in County Kildare, Republic of Ireland. No artificial light, photoperiodic treatments or chemical treatments were given to the plants. Measurements and numerical values represent averages of typical plant types.

Botanical classification: *Potentilla fruticosa* 'KM01'.

PROPAGATION

Type: Vegetative cuttings.

Time to initiate roots: Approximately 14 days at 20° C.

Time to develop roots: Approximately 40 days at 20° C.

Root description: Fine, fibrous, freely branching; brown in color.

PLANT

Age of plant described: Approximately 3 years old from a rooted cutting.

Growth habit: Hardy, perennial, deciduous shrub; upright and outwardly spreading plant habit, roughly globular in shape.

Height: Approximately 36 cm.

Plant spread: Approximately 60 cm.

Growth rate: Moderately vigorous.

Branching characteristics: Freely branching. Usually about 35 lateral branches develop per plant; pinching enhances lateral branch development.

Lateral branch:

*Length*.—About 22 cm.
*Diameter*.—About 2 mm.
*Internode length*.—About 1.3 cm.
*Strength*.—Strong.
*Texture*.—Pubescent, rough; woody with age.
*Color, developing*.—Upper side: Near RHS Greyed-Red 182B. Lower side: Near RHS Yellow-Green 145B.
*Color, woody*.—Near Brown RHS 200C.

FOLIAGE

Leaf:

*Arrangement*.—Alternate; palmately compound with five leaflets per leaf. Leaflets sessile.
*Average leaf length*.—Approximately 2.4 cm.
*Average leaf width*.—Approximately 2.5 cm.
*Average leaflet length*.—Approximately 1.4 cm.
*Average leaflet width*.—Approximately 0.5 cm.
*Shape of leaflet*.—Narrowly obovate to elliptic.
*Leaflet apex*.—Short apiculate.
*Leaflet base*.—Attenuate.
*Leaflet margin*.—Entire.
*Leaflet texture of top surface*.—Sparsely pubescent.
*Leaflet texture of bottom surface*.—Sparsely pubescent.
*Leaflet venation pattern*.—Pinnate.
*Color*.—Young foliage upper side: Near RHS Yellow-Green 146A. Venation near RHS Green 138A. Young foliage under side: Near RHS Yellow-Green 144A. Venation near RHS Green 138A. Mature foliage upper side: Near RHS Yellow-Green 147A. Venation near RHS Green 137A. Mature foliage under side: Near RHS Green 138B. Venation near RHS Green 137A.

Petiole:

*Length*.—Approximately 0.5 cm.
*Diameter*.—Approximately 0.6 mm.
*Texture*.—Smooth, glabrous.
*Color, upper and lower surfaces*.—Near RHS Green 138D.

FLOWER

Natural flowering season: Plants begin flowering about 8 months after planting and flower from early Summer until late Autumn in Ireland.

Flower arrangement, shape and habit: Single rotate flowers. Flowers usually terminal and in groups of 3 to 5. Flower face upward and freely flowering habit.

Flower longevity on plant: About 4 days.

Quantity of flowers: About 12 flowers and flower buds per lateral branch.

Flowers persistent or self cleaning: Not persistent.

Fragrance: None detected.

Flower size:

*Diameter*.—Approximately 30 mm.
*Depth*.—Approximately 5 mm.

Petals:

*Petal arrangement*.—5, in a single whorl.
*Margin*.—Entire.
*Apex*.—Obtuse.
*Length*.—Approximately 1.2 cm.
*Width*.—Approximately 1.2 cm.
*Shape*.—Orbicular, slightly concave.
*Base*.—Attenuate.
*Texture*.—Smooth, glabrous.
*Aspect*.—Upright and bending outward.
*Color*.—When opening: Base: Near Orange-White RHS 159A. Apex: Near Greyed-Red RHS 182D. Fully opened: Upper surface: Center Near Yellow-Orange RHS 21C; Edges near Red RHS 37A. Lower surface: Near Yellow RHS 10B.

Bud:

*Shape*.—Broadly Ovate.
*Length*.—Average 4 mm.
*Diameter*.—Average 6 mm.
*Color*.—Near Yellow-Green RHS 149A.

Sepals:

*Quantity*.—5, in a single whorl.
*Shape*.—Oblanceolate.
*Length*.—Approximately 9 mm.
*Width*.—Approximately 2 mm.
*Margin*.—Entire.
*Apex*.—Acute.
*Base*.—Cuneate.
*Texture*.—Smooth, glabrous.
*Color* (*immature and mature*).—Upper surface: Near Yellow-Green RHS 147A. Lower surface: Near Yellow-Green RHS 147B.

Pedicels:
*Length*.—Average 4 cm.
*Diameter*.—About 0.75 mm.
*Color*.—Near Yellow-Green RHS 145D.
*Aspect*.—Erect.
*Texture*.—Smooth, glabrous.

REPRODUCTIVE ORGANS

Stamens:
*Number*.—Approximately 27.
*Filament length*.—Approximately 1.5 mm.
Anthers:
*Shape*.—Ovate.
*Size*.—Approximately 1 mm. by 0.75 mm.
*Color*.—Near Yellow RHS 13B.
*Pollen*.—Amount: Scarce. Color: Near Yellow RHS 13B.
Pistil:
*Number per flower*.—Approximately 30.
*Length*.—Approximately 2 mm.
*Style*.—Length: Approximately 1 mm. Color: Near Yellow-Green RHS 154B.
Stigma:
*Color*.—Near Yellow-Green RHS 154B.
*Ovary color*.—Near Yellow-Green RHS between 145C and 145D.

OTHER CHARACTERISTICS

Disease resistance: Has not shown to offer any improved resistance to know pathogens and pest of *Potentilla*.
Drought tolerance and cold tolerance: Hardy to USDA Hardiness zone 3. Tolerant of high temperatures to at least 35° C.
Fruit/seed production: Not observed to date.

What is claimed is:

1. A new and distinct cultivar of *Potentilla fruticosa* plant named 'KM01' as herein illustrated and described.

* * * * *